United States Patent [19]
Feibus

[11] Patent Number: 5,053,021
[45] Date of Patent: Oct. 1, 1991

[54] SURGICAL DRAIN

[76] Inventor: Miriam H. Feibus, 2557 Morrocroft La., Charlotte, N.C. 28211

[21] Appl. No.: 460,782

[22] Filed: Jan. 4, 1990

Related U.S. Application Data

[63] Continuation-in-part of Ser. No. 348,324, May 5, 1989, Pat. No. 4,970,109, which is a continuation-in-part of Ser. No. 132,122, Dec. 14, 1987, Pat. No. 4,856,299, which is a continuation-in-part of Ser. No. 940,864, Dec. 12, 1986, Pat. No. 4,815,299.

[51] Int. Cl.$^5$ ................................................ A61M 5/00
[52] U.S. Cl. ........................................ 604/264; 66/195; 66/202; 428/242; 428/253; 428/283; 428/913
[58] Field of Search ............... 604/264; 428/253, 242, 428/283, 913; 66/195, 202; 57/901; 361/210, 212, 220; 174/117 M

[56] References Cited

U.S. PATENT DOCUMENTS

| | | | |
|---|---|---|---|
| 3,957,054 | 10/1976 | McFarlane | 604/282 |
| 4,139,012 | 11/1980 | Zahorsky | 604/268 |
| 4,217,904 | 12/1980 | Zahorsky | 604/268 |
| 4,422,483 | 8/1983 | Zins | 139/420 R |

Primary Examiner—James J. Bell
Attorney, Agent, or Firm—Kenyon & Kenyon

[57] ABSTRACT

The present invention relates to a surgical drain fabric and surgical drain device for providing a channel of exit or discharge from a wound or wound cavity and, more specifically, a fabric in the form of a tape having finished longitudinal edges useful for drawing wound drainage out of a patient's body. Preferably, the fabric is knitted in the form of a tape comprised of conductive yarns and nonconductive yarns stitched in a single warp and single weft pattern so as to provide enhanced drainage characteristics. The yarns and knit stitch are chosen to minimize the danger of sluffing and linting and other disadvantages associated with previous surgical drain materials.

16 Claims, 4 Drawing Sheets

SURGICAL DRAIN

BACKGROUND OF THE INVENTION

This is a continuation in part application of U.S. application No. 348,324 (barrier cloth), filed May 5, 1989, now U.S. Pat. No. 4,970,109 which is a continuation in part application of U.S. application Ser. No. 132,122, filed Dec. 14, 1987 and now U.S. Pat. No. 4,856,299, which is a continuation in part application of U.S. application No. 940,864, filed Dec. 12, 1986, now U.S. Pat. No. 4,815,299.

FIELD OF THE INVENTION

This invention relates to an appliance or material which provides a channel of exit or discharge from a wound cavity and, more specifically, to a fabric, preferably in tape form, comprised of electrically conductive yarns and nonconductive yarns that allows the removal of discharge from a wound cavity.

DESCRIPTION OF THE PRIOR ART

The therapeutic effect of promoting drainage from wound cavities is well known and has been the subject of a number of devices to promote such drainage. These devices which afford a channel of exit or discharge from a wound cavity have come in many forms, but may be classified generally in three groups.

The first general group, employ a hollow structure, such as a tube, which is placed in the wound to allow the removal of wound discharge by, e.g., capillary action and/or siphonage and/or gravity. A number of these "tube" type drains have also been used in conjunction with vacuum producing apparatus to assist drainage. Advantages shared by tube-type surgical drains are, for example, 1) ease of insertion into a wound cavity and 2) their drainage function is not generally affected by the volume of discharge. Further, since they provide constant drainage, the need to replace them is significantly reduced. There are, however, a number of disadvantages of tube-type surgical drains, including, for example, the difficulties of avoiding infection and promoting healing inherent in a device inserted in a wound cavity that is nondegradable. In addition, tube-type surgical drains tend to be prone to blockage and other forms of obstruction, e.g., when the tube opening contacts body tissue the passage of discharge may be obstructed.

The second general group, of surgical drain devices, include those made of various forms of fibers and fabrics having absorptive properties, which are placed in a wound cavity to allow removal of wound discharges, e.g., by absorption. Advantages shared by these "fabric" type surgical drains are that they can be relatively easily sized and manipulated regardless of the size of the wound cavity and they are less prone to blockage or obstruction than tube-type drains. As with tube-type drains, fabric-type drains suffer from a number of disadvantages, such as susceptibility to sluffing or linting, which may promote irritation and associated infection, and their drainage capacity maybe limited to the fluid retention capacity of the fabric, i.e., the drainage is not continuous. Drainage capacity problems may be aggravated by using hydrophilic fibers, e.g., cellulose derived and yarns, due to their water binding properties. A consequence of the drainage capacity limitation is that fabric-type surgical drains must ordinarily be replaced on relatively short intervals.

Further, conventional fabric-type drain materials are often so loosely woven that they fragment which increases the risk of infection. Moreover, natural fibers like cotton, and other cellulosics, are themselves prone to sluffing small fragments that also increase the risk of infection. In addition, depending on the fibers selected, known fabric-type surgical drains may decompose over time, again necessitating more frequent replacement, and, not uncommonly, debriding of the wound cavity. Another limitation of known fabric-type surgical drains is that, once positioned, they may be difficult to relocate or retrieve.

The third general group, of surgical drain devices, is a hybrid of the above described tube-type and fabric-type drains including both a hollow structure and absorptive fibers. In these combination-type surgical drains, a fabric is usually either wrapped around or arranged within a hollow structure to form a composite which may be inserted into a wound. Combination-type drains enjoy some of the advantageous properties of both tube- and fabric-type drains. While this type of drain has the advantage of ease of manipulation and may have better drainage characteristics than the other general types of surgical drains, it may also suffer from their disadvantages.

An example of a combination-type drain routinely used in surgical procedures, is made from gauze, e.g., a loosely woven cotton fabric, which may be layered and cut to size and then placed in either surgical sheathing or a tubular part cut from a rubber glove prior to insertion into a wound cavity. The surgical sheathing or rubber glove part is used to prevent loose fragments or threads of the gauze from entering the wound cavity. Gauze is prone to fragmenting and leaves many loose threads when it is cut and additional parts of the fabric may fall away under minimal pressure, i.e., sluffing and linting. The use of the sheath or glove to limit such sluffing and linting, however, is not completely effective or convenient for use in an operating room setting. Furthermore, drainage with this type of surgical drain may be limited to the fluid retention capacity of the fabric and a small amounts of evaporation.

Other known surgical drains, include 'cigarette drains', made by surrounding a strip of gauze with a protective covering of rubber, gutta-percha, or the like; and 'Mikulicz' drains' formed by pushing a single layer of gauze into a wound cavity, the layer of gauze being packed with several thick wicks of gauze as it is pushed into the cavity. As with other known surgical drains, these drains suffer from disadvantages, including susceptibility to sluffing or linting, and that their drainage capacity may be limited to the fluid retention capacity of the fabric.

U.S. Pat. No. 3,957,054, issued to McFarlane, describes a tube-type drain which is flexible and pliable and comprises a plurality of ribs arranged in such a fashion about the interior of the column of the tube so that the tube cannot be collapsed.

U.S Pat. No. 4,139,012, and its continuation, U.S. Pat. No. 4,217,904, both issued to Zahorsky, describe surgical drain tubes having a construction said to minimize the problem of clogging found in known tube designs via a protective shield member.

Other known surgical drains are described in U.S. Pat. Nos. 4,257,422; 4,551,141; 4,623,329; 4,315,509;

4,579,555; 4,080,970; 4,781,678; 4,692,153; 4,523,920; 4,654,032; and 4,508,533.

A need exists, therefor, for a relatively inexpensive and easily manufactured surgical drain capable of providing drainage without some of the disadvantages of known surgical drains such as clogging, sluffing, linting, and decomposition. In addition, a desired surgical drain fabric should provide drainage for extended periods that is not limited to the fluid retention capacity of the fabric or evaporation time.

ADVANTAGES AND SUMMARY OF THE INVENTION

It is an advantage of the present invention to provide a readily manufactured surgical drain fabric, preferably in the form of a tape having finished edges and comprised of conductive yarns and nonconductive yarns stitched together so as to provide absorptive properties without the sluffing or linting associated with known surgical drain fabrics.

It is yet another advantage of the present invention to provide a surgical drain fabric that can be sterilized by conventional processes and is comprised of conductive yarns, nonconductive yarns and a radio opaque means; so that the resulting fabric is radiographically visible and thereby can be readily positioned and repositioned without further exploratory surgery or otherwise intrusive procedures.

It is still another advantage of the present invention to provide a surgical drain in the form of a fabric tape drawn through a plastic tube that is easy to use and provides improved drainage without the dangers of clogging, linting or sluffing.

The present invention provides a surgical drain fabric which comprises conductive and nonconductive yarns stitched together to form a fabric tape having finished longitudinal edges wherein the conductive yarns form an electrically conductive matrix.

The invention also provides a surgical drain comprising a hollow member having disposed therein a fabric comprised of conductive and nonconductive yarns stitched together so that the conductive yarns form an electrically conductive matrix.

The invention also embraces methods for making and using both the surgical drain fabric and surgical drain described above.

While not wishing to be bound by any particular theory of invention or mode of action it appears the fabrics of this invention made with synthetic yarns have improved drainage properties because the fibers in synthetic yarns tend to be hydrophobic and therefore they do not bind body fluids (water) in the way that cellulosic fibers do. Bound fluid inhibits drainage because it limits the amount and rate of fluid that can pass through the fabric.

BRIEF DESCRIPTION OF THE DRAWINGS

The above and other features and advantages of the present invention will become apparent from the discussion hereinbelow of specific, illustrative embodiments thereof presented in conjunction with the accompanying drawings, in which.

DESCRIPTION OF THE PREFERRED EMBODIMENTS

Figure 1:
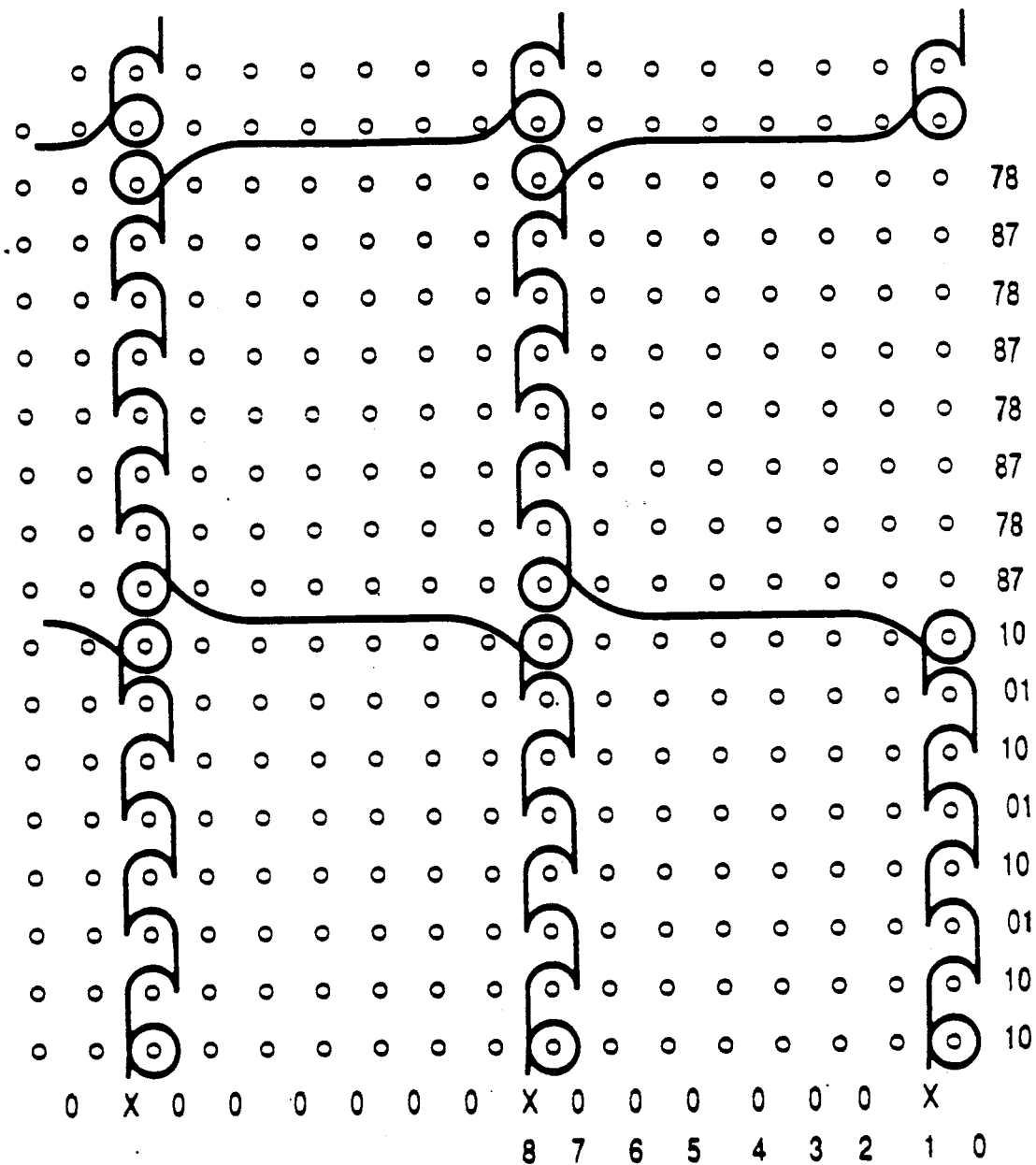
FIG. 1 is a point diagram which depicts a knitted stitch pattern showing a conductive yarn arrangement of the present invention.

Referring to FIG. 1, the illustrated sequence of knitted chain stitches may be formed on a knitting machine of the type well known in the art. See, e.g., "An Introduction to the Stitch Formations in Warp Knitting" § 1.3, pp. 2742 (Employees Assoc. Karl Mayer E.V., West Germany 1966) and the knitting machine described in U.S. Pat. Nos. 4,856,299 and 4,185,299, assigned to the same assignee as the present invention, the texts of which are incorporated herein by reference. Preferred machines for making surgical drain fabric tape are jaquard knitting machines, e.g., a Jacob Mueller, R.B.J.K 14 gauge machine.

Figure 2A:
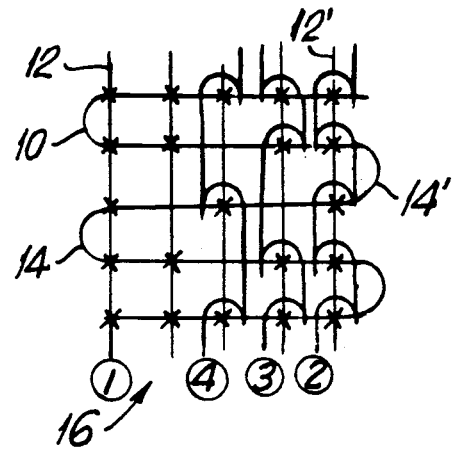
FIGS. 2A-2D illustrates alternatively stitch patterns for the present invention.
Figure 2C:
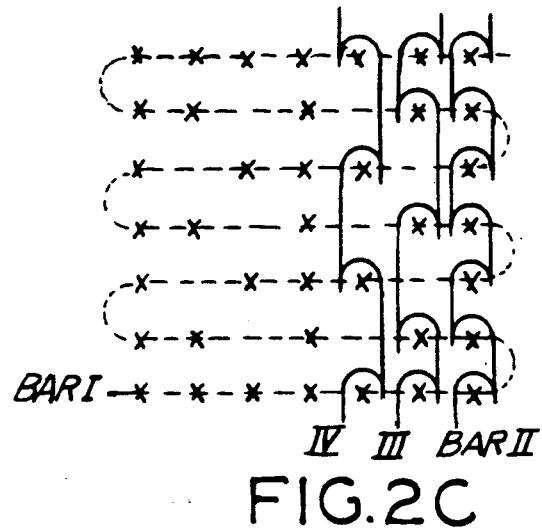
Figure 2B:
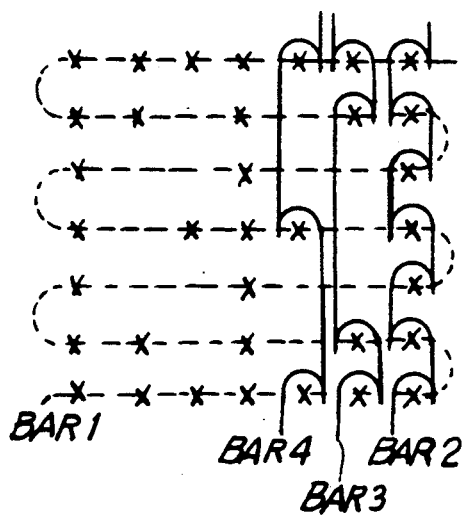
Figure 2D:
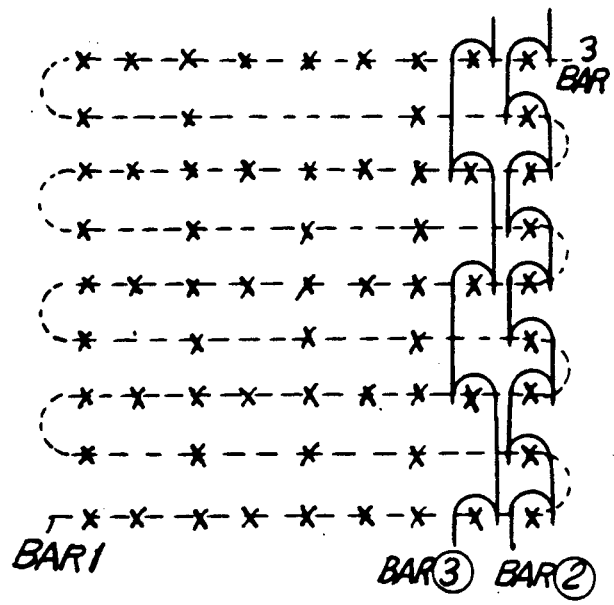
Figure 3:
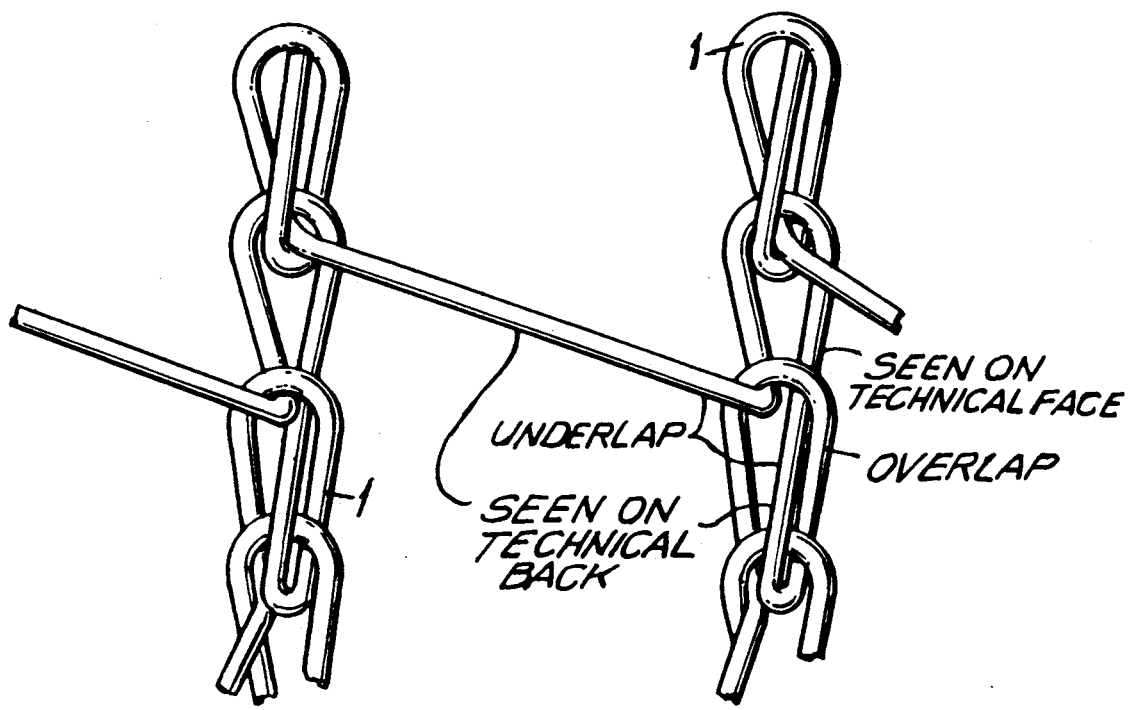
FIG. 3 depicts an enlarge section of the stitch pattern shown in FIG. 1 illustrating the arrangement of conductive fiber 1 extending along the course and wale directions and which forms overlaps and underlaps within the fabric.

FIGS. 2A to 2D illustrate alternative stitch patterns for a surgical tape fabric 16 constructed in accordance with the invention and FIG. 3 is an enlarged section of knitted fabric illustrating chain stitch in modified Queen's Cord construction. As in FIG. 2 the continuous weft yarn 10 wraps around the outermost warp yarns 12 and 12' forming opposing finished longitudinal edges 14 and 14'. The term finished edge means that the marginal edges of the fabric are substantially free of loose yarn ends that are susceptible to breaking away from the fabric. Those skilled in the art will appreciate that selvedging, bonding and similar known techniques can be employed to finish edges on alternative fabric constructions.

It should be appreciated that the surgical drain fabric of this invention can be any knitted, woven or nonwoven material of staple or mono- or multifilant yarns that includes an electrically conductive matrix and is stitched or bonded together forming a fabric that will provide effective wound drainage over extended periods of time, e.g., up to 2 or more days. The preferred form for the fabric is a tape or ribbon having finished longitudinal edges. Tapes can be knitted or woven with finished edges or cut from sheets followed by finishing the edges. Preferably, the tape width is in the range of about 5 to 25 mm. The surgical drain fabric tape may be cut into pieces having a length sufficient to have one end thereof drawn through tube 42 to the vicinity of discharge connector 44 while leaving at least about 1 cm of the fabric 16 ends extending from the end 45 of tube 42 as shown in FIG. 4, and described in greater detail below.

The nonconductive yarn used to make the surgical drain fabric of this invention can be any of the well known biocompatible yarns; and preferably is a monofilament or multi-filament synthetic yarn such as a texturized polyester, e.g., UNIFI 1-150-50, (20 to 200 denier). Polyesters are preferred because they are not easily degraded by body fluids or medicaments. Other available yarns, such as, microfilaments available from UNIFI 1-150-100 and DuPont may be advantageously incorporated in this product. Staple yarns should be avoided because staple fibers can sluff-off in use and may cause infection. The conductive yarns are preferably monofilament or multifilaments made of any electrically conductive material, e.g., see: U.S. Pat. No. 4,422,483. Preferred conductive yarns are carbon yarns available from BASF Type 191 (20 to 200 denier).

The surgical drain fabric of this invention can also be folded, rolled wrapped or otherwise formed in to a wad or sponge useful in medical procedures especially dental procedures for collecting excess liquid such as blood or saliva.

Figure 4:
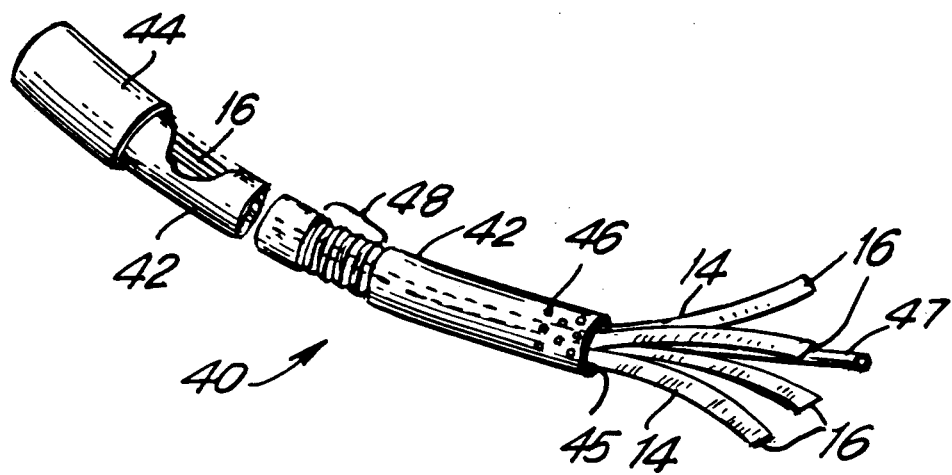
FIG. 4 illustrates a surgical drain constructed in accordance with the invention.
Figure 5:
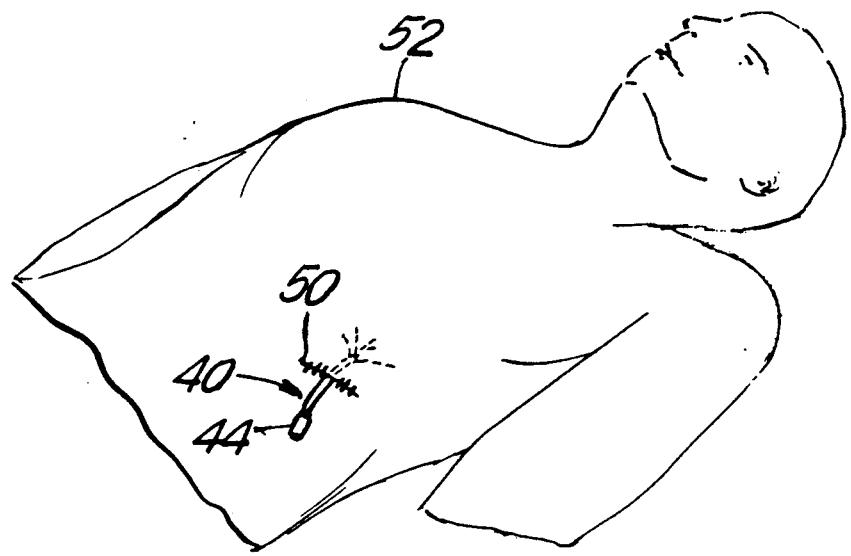
FIG. 5 illustrates the surgical drain of FIG. 4 implanted in a wound.

The surgical drain 40, shown in FIG. 4, is a biocompatible plastic tube 42 preferably having a discharge connector 44 disposed at one end thereof for attachment to a drainage bag (not shown) or similar means for collecting wound drainage. Of course, discharge connector 44 could be attached to a vacuum assist device or simply left open. The opposing end 45 of tube 42 may be provided with perforations 46 to aid in collection of wound drainage. The tube 42 may be rigid or flexible, as dictated by particular applications, and may also include one or more flexing sections 48 to provide bending at desired locations. In addition or alternatively, a bendable wire 47 can be passed through the tube 42 so that the drain 40 can be bent to any desired angle for selected applications. Preferably, the wire 47 is copper, silver, gold or other material having antimicrobial properties. It may also be advantageous to treat the fabric 16 and/or tube 42 with known antimicrobial agents to reduce the risk of infection and/or to apply antithrombogenic agents to the tube 42 or portions thereof, such as, heparin or sodium citrate. Surgical drain 40 is shown extending from wound 50 in patient 52 in FIG. 5.

The tube 42 which encloses the surgical drain fabric 16 can be made of any biologically acceptable material, synthetic plastics being preferred. The tube may be as rigid as a drinking straw or flexible as the finger of a latex surgical glove. Tube structures are easily formed by conventional plastic working processes such as extrusion.

EXAMPLE 1

An example of a non-linting and non-sluffing knitted fabric tape of the present invention was constructed as follows on a Jakob Mueller R.B.J.K. 14 gauge, i.e., 20.3 stitches to the inch, jacquard knitting machine. This particular embodiment of the tape was constructed on a pattern of five as shown in FIG. 2A, in the following manner:

a single warp consisting of three yarns, that is, two conductive yarns* each comprising 2 70 denier polyester filaments and conductive nylon filament and the third yarn is a UNIFI type 1-150-50 texturized polyester.

*BASF Type 191

1 weft yarn of UNIFI type 1-150-50 texturized yarn knitted continuously back and forth.

The numerical representation of this pattern is:
Bar 1 5-5, 0-0
Bar 2 1-0, 0-1, 1-0, 0-1, 1-0
Bar 3 1-0, 0-1, 1-1, 1-0, 0-1
Bar 4 1-0, 0-0, 0-1, 1-1, 1-0

As a result, the interlocking conductive stitches, using the weft end for support, form a continuous "box" pattern with a conductive yarn connecting of the four corners of each box. This pattern is important as it tends to distribute the conductive yarns evenly throughout the fabric enhancing the drainage capacity. Thus, a relatively loosely packed fabric is achieved by using only a single weft thread for support, with a result that the drainage rate is increased. Further, as the fabric may be dispensed in, e.g., a tape dispenser, and then cut to a desired length by a physician, the box pattern provides finished edges so that no loose threads result from cutting the fabric tape across its width. As previously discussed, the lack of loose threads reduces the chance of infection.

The result of the above procedure is a finished edge fabric or "tape" that is of approximately ⅜ (7.5 mm) in width and can be made into any desired length. The knitted surgical drain fabric of the present invention may then be treated by the steps of:

1. Scouring, e.g., boiling, the tape; and
2. Heat setting the scoured tape at about 350 degrees Fahrenheit.

As will be appreciated, a benefit of the "box" pattern of the present invention is that no additional mechanical finishing, e.g., sewing or burning of the fabric's edges is needed to bind loose threads.

EXAMPLE 2

In order to achieve wider surgical tapes, the same jacquard knitting machine can be utilized in substantially the same manner as described in Example 1 to produce the following patterns corresponding to FIGS. 2B, 2C and 2D:

2B

Bar 1 7-7, 0-0
Bar 2 1-0, 0-1, 1-0, 0-1, 1-0, 0-1, 1-0
Bar 3 1-0, 0-1, 1-1, 1-1, 1-1, 1-0, 0-1
Bar 4 1-0, 0-0, 0-0, 0-1, 1-1, 1-1, 1-0

2C

Bar 1 7-7, 0-0
Bar 2 1-0, 0-1, 1-0, 0-1, 1-0, 0-1, 1-0
Bar 3 1-0, 0-1, 1-1, 1-0, 0-0, 0-1, 1-0
Bar 4 1-0, 0-0, 0-1, 1-1, 1-0, 0-0, 0-1

2D

Bar 1 9-9, 0-0
Bar 2 1-0, 0-1, 1-0, 0-1, 1-0, 0-1, 1-0, 0-1, 1-0
Bar 3 1-0, 0-0, 0-1, 1-1, 1-0, 0-0, 0-1, 1-1, 1-0, repeat

As will be appreciated by those skilled in the art in reviewing patterns 2A, 2B, 2C and 2D, a large number of knit patterns are possible as long as a continuous matrix of conductive yarn is provided.

It has also been discovered that a hydrophobic fabric, such as that used in the present invention, can drain more quickly, i.e., begin to move blood sooner if the fabric is pre-wet with a liquid such as, for example, water or mixtures of water and alcohol particularly 1 to 5% vol. aqueous isopropyl (rubbing) alcohol. In a preferred embodiment, the fabric tape drain is pre-wetted with an alcohol-water solution.

EXAMPLE 3

An alcohol-water solution comprising 10 cc of isopropyl alcohol in 200 cc of distilled water was used to wet fabric tapes constructed in accordance with the present invention. Three samples of fabric tapes prepared in accordance with example 1 were run concurrently, with each tape measuring approximately 25 cm in length. Tape No. 1 comprised a fabric tape which had been totally immersed in the alcohol-water solution so that it became wet. Tape No. 2 comprised a dry fabric tape. Tape No. 3 comprised a fabric tape that was damp, not wet, with the alcohol-water solution.

In the first test "A", 6 cc of Povidone ™ iodine prep solution (which is quite viscous and has a tendency to dry rapidly) was placed in three separate glass tubes. One end of each tape was submerged in the Povidone and the opposite end draped over the side of the glass tube into a collection vessel. The volume of liquid in each collection vessel was periodically measured and the results are summarized in Table I.

In the second test "B", fabric tapes were wet with sterilized water the first sample tape 1 was soaked; the second sample tape 2 was dry and the third sample tape 3 was damp only. The three sample tapes were used to drain Povidone as in Test A and the results are also summarized in Table I, wherein the cumulative amount of fluid drained (in cubic centimeters "cc") over a given period is illustrated.

TABLE 1

| Tape | 18 minutes | 40 minutes | 65 minutes |
|---|---|---|---|
| A. Povidone iodine prep solution. | | | |
| 1. | 0.75 cc | 1.75 cc | 2.75 cc |
| 2. | 1.0 cc | 2.0 cc | 2.75 cc |
| 3. | 0.5 cc | 1.0 cc | 1.5 cc |
| Tape | 22 minutes | 50 minutes | |
| B. Sterilized water. | | | |
| 1. | 1.0 cc | 1.5 cc | |
| 2. | 1.0 cc | 1.5 cc | |
| 3. | 1.0 cc | 1.25 cc | |

It should be appreciated that a surgical drain fabric tape of the present invention may be autoclave and gamma ray sterilized and may be hypoallergenic depending on the choice of material used to make the fabric and/or tube. In addition, were the tape to be enclosed in a surgical sheath, the physician would have the flexibility to increase or decrease the rapidity of drainage, or even change the drain altogether from outside the patients body.

It should be understood that this invention is not limited to the illustrations described and shown herein, which are deemed to be merely illustrative of various modes of carrying out the invention.

I claim:

1. A surgical drain warp knitted fabric which comprises a knit structure of conductive and nonconductive yarns stitched together to form a fabric tape wherein the conductive yarns make electrical contact with one another so as to form an electrically conductive matrix.

2. The fabric tape of claim 1, wherein the yarns are knitted together in a single weft single warp pattern.

3. The fabric of claim 1 wherein the conductive yarns are chosen from the group consisting of carbon suffused nylon; filamentary polymer substrates having finely divided, electrically-conductive particles embossed on the fiber surface; and graphite fibers.

4. The fabric of claim 3 wherein the conductive yarns consist of two or more conductive fibers plied together.

5. The fabric of claim 3 wherein the conductive yarns consist of a conductive fibers plied together with a nonconductive fiber.

6. The fabric of claim 3 wherein the conductive yarn is trapped between the overlaps and underlaps of the nonconductive yarn in the fabric as seen from the technical back.

7. A surgical drain comprising a hollow member having disposed therein a warp knitted fabric comprised of conductive and nonconductive yarns stitched together so that the conductive yarns make electrical contact with one another so as to form an electrically conductive matrix.

8. The drain of claim 7, wherein the fabric is in tape form having finished longitudinal edges.

9. The drain of claim 8, wherein the yarns are knitted together in a single weft single warp pattern.

10. The drain of claim 8, wherein the conductive yarns are chosen from the group consisting of carbon suffused nylon; filamentary polymer substrates having finely divided, electrically-conductive particles embossed on the fiber surface.

11. The drain of claim 8, wherein the conductive yarn is trapped between the overlaps and underlaps of the nonconductive yarn as seen from the technical back.

12. The fabric tape of claim 1 having finished longitudinal edges.

13. A knitted fabric for a surgical drain fabricated by threading a four Bar 20.3 stitch to the inch jacquard knitting machine in a pattern of five comprising:

a single warp consisting of three yarns, including two conductive yarns, each comprising two 70 denier polyester filaments and a conductive nylon filament, and a third yarn comprising a UNIFI type 1-150-50 texturized polyester;

a single weft yarn of UNIFI type 1-150-50 texturized yarn knitted continuously back and forth in the following sequence for Bar 1:
5-5, 0-0
the following sequence for Bar 2:
1-0, 0-1, 1-0, 0-1, 1-0
the following sequence for Bar 3:
1-0, 0-1, 1-1, 1-0, 0-1
and the following sequence for Bar 4:
1-0, 0-0, 0-1, 1-1, 1-0.

14. The knitted fabric for a surgical drain of claim 13 wherein the single weft yarn of UNIFI type 1-150-50 texturized yarn is knitted continuously back and forth in the following sequence for Bar 1:
7-7, 0-0
the following sequence for Bar 2:
1-0, 0-1, 1-0, 0-1, 1-0, 0-1, 1-0
the following sequence for Bar 3:
1-0, 0-1, 1-1, 1-1, 1-1, 1-0, 0-1
and the following sequence for Bar 4:
1-0, 0-0, 0-0, 0-1, 1-1, 1-1, 1-0.

15. The knitted fabric for a surgical drain of claim 13 wherein the single weft yarn of UNIFI type 1-150-50 texturized yarn is knitted continuously back and forth in the following sequence for Bar 1:
7-7, 0-0
the following sequence for Bar 2:
1-0, 0-1, 1-0, 0-1, 1-0, 0-1, 1-0
the following sequence for Bar 3:
1-0, 0-1, 1-1, 1-0, 0-0, 0-1, 1-0
and the following sequence for Bar 4:
1-0, 0-0, 0-1, 1-1, 1-0, 0-0, 0-1.

16. The knitted fabric for a surgical drain of claim 13 wherein the single weft yarn of UNIFI type 1-150-50 texturized yarn is knitted continuously back and forth in the following sequence for Bar 1:
9-9, 0-0
the following sequence for Bar 2:
1-0, 0-1, 1-0, 0-1, 1-0, 0-1, 1-0, 0-1, 1-0
the following sequence for Bar 3:
1-0, 0-0, 0-1, 1-1, 1-0, 0-0, 0-1, 1-1, 1-0, repeat.

* * * * *